US012447330B2

(12) United States Patent
Yin et al.

(10) Patent No.: US 12,447,330 B2
(45) Date of Patent: Oct. 21, 2025

(54) ELECTRODE STRUCTURE FOR ELECTRONIC MUSCLE STIMULATION

(71) Applicant: TAIWAN TEXTILE RESEARCH INSTITUTE, New Taipei (TW)

(72) Inventors: Chieh Yin, New Taipei (TW); Chien-Lung Shen, New Taipei (TW); Chien-Fa Tang, New Taipei (TW); Ching Yeh, New Taipei (TW)

(73) Assignee: TAIWAN TEXTILE RESEARCH INSTITUTE, New Taipei (TW)

( * ) Notice: Subject to any disclaimer, the term of this patent is extended or adjusted under 35 U.S.C. 154(b) by 375 days.

(21) Appl. No.: 18/164,662

(22) Filed: Feb. 6, 2023

(65) Prior Publication Data

US 2024/0066285 A1 Feb. 29, 2024

(30) Foreign Application Priority Data

Aug. 24, 2022 (TW) ................................. 111131858

(51) Int. Cl.
*A61N 1/04* (2006.01)
*A61N 1/36* (2006.01)

(52) U.S. Cl.
CPC ......... *A61N 1/0484* (2013.01); *A61N 1/0452* (2013.01)

(58) Field of Classification Search
CPC .. A61N 1/0484; A61N 1/0452; A61N 1/0476; A61N 1/0492; A61N 1/0472; A61N 1/36003; A61N 1/36014; A61N 1/0496; A61N 1/3603; A61N 1/36031; A61N 1/36034; A61N 1/0404; A61N 1/08; A61B 5/389; A61B 5/4519
See application file for complete search history.

(56) References Cited

U.S. PATENT DOCUMENTS

| | | | | |
|---|---|---|---|---|
| 4,722,354 | A * | 2/1988 | Axelgaard | D04B 1/14 607/152 |
| 9,981,120 | B2 | 5/2018 | Buhlmann et al. | |
| 11,253,203 | B2 | 2/2022 | Yang | |
| 2003/0176908 | A1 * | 9/2003 | Lin | A61N 1/0492 607/142 |
| 2014/0209351 | A1 * | 7/2014 | Reinhardt | A61N 1/0452 174/126.2 |
| 2017/0056644 | A1 * | 3/2017 | Chahine | A61N 1/36014 |
| 2018/0147404 | A1 * | 5/2018 | Nagel | A61N 1/0452 |
| 2020/0069934 | A1 * | 3/2020 | Mistretta | A61N 1/0452 |
| 2021/0244332 | A1 | 8/2021 | Hagihara et al. | |

FOREIGN PATENT DOCUMENTS

WO 2013075270 A1 5/2013

* cited by examiner

*Primary Examiner* — Carl H Layno
*Assistant Examiner* — Anh-Khoa N Dinh
(74) *Attorney, Agent, or Firm* — McClure, Qualey & Rodack, LLP

(57) ABSTRACT

An electrode structure for electronic muscle stimulation (EMS) includes a conductive fabric layer, a water retention fabric layer, and an insulation cover. The conductive fabric layer has a first surface and a second surface opposite to each other. The water retention fabric layer is connected to the first surface of the conductive fabric layer, in which the EMS points of the electrode structure are consisted of the water retention fabric layer. The insulation cover is disposed on the first surface of the conductive fabric layer and surrounding the edges of the water retention fabric layer.

9 Claims, 7 Drawing Sheets

ELECTRODE STRUCTURE FOR ELECTRONIC MUSCLE STIMULATION

RELATED APPLICATIONS

This application claims priority to Taiwanese Application Serial Number 111131858, filed Aug. 24, 2022, which is herein incorporated by reference.

BACKGROUND

Field of Invention

The present invention relates to an electrode structure for electronic muscle stimulation (EMS).

Description of Related Art

Many disease patients and surgery patients have requirements of exercise rehabilitation therapy. The exercise rehabilitation therapy is preferably made within the golden rehabilitation period to achieve good performance. For example, functional electrical stimulation (FES) is an active rehabilitation type, which introduces current under skin to occur muscle contraction thereby increasing functional activities of extremities.

The traditional electronic muscle stimulation (EMS) electrodes are disposable electrodes which cannot be multiple used and pollute the environment. Recently, textile electrodes which can be multiple used are well developed. The conductive fibers in the textile electrodes are utilized to contact the wearer's skin to generate muscle stimulation. However, due to the uneven conductive paths of the conductive fibers in the textile electrodes, the EMS points of the textile electrodes have uneven resistances, and the voltage potentials of the EMS points of the textile electrodes are different. Therefore, the wearer may feel spike and uncomfortable while using the textile electrodes.

SUMMARY

An aspect of the disclosure provides an electrode structure for electronic muscle stimulation (EMS). The electrode structure includes a conductive fabric layer, a water retention fabric layer, and an insulation cover. The conductive fabric layer has a first surface and a second surface opposite to each other. The water retention fabric layer is connected to the first surface of the conductive fabric layer, in which the EMS points of the electrode structure are consisted of the water retention fabric layer. The insulation cover is disposed on the first surface of the conductive fabric layer and surrounding the edges of the water retention fabric layer.

According to some embodiments of the disclosure, the electrode structure has a surface resistance ranging from 30 kΩ to 100 kΩ, after the electrode structure absorbs moisture.

According to some embodiments of the disclosure, the electrode structure has an EMS current ranging from 1 mA to 100 mA.

According to some embodiments of the disclosure, the electrode structure further includes a dielectric isolation layer disposed on the second surface of the conductive fabric layer.

According to some embodiments of the disclosure, the electrode structure further includes a conductive contact penetrating the dielectric isolation layer and connecting to the conductive fabric layer such that a voltage is applied to the conductive fabric layer via the conductive contact.

According to some embodiments of the disclosure, the water retention fabric layer and the conductive fabric layer are interconnected by a plurality of water retention yarn loops of the water retention fabric layer and a plurality of conductive yarn loops of the conductive fabric layer, and the conductive yarn loops are completely hidden under the water retention yarn loops.

According to some embodiments of the disclosure, the conductive fabric layer is a fabric comprising conductive yarns or metal wires, or a non-woven fabric coated with a conductive layer.

According to some embodiments of the disclosure, the water retention fabric layer comprises cotton fibers, modified nylon fibers, alginate fibers, or combinations thereof.

According to some embodiments of the disclosure, the dielectric protection layer comprises silicon or elastic plastic.

According to some embodiments of the disclosure, a moisture transferring ability of the water retention fabric layer is greater than level 4, following FTTS-FA-004 test method.

The present disclosure provides an electrode structure to gently and indirectly transfer an external voltage to the wearer's skin. The EMS points of the electrode structure are consisted of the water retention fabric layer. The external voltage enters the conductive fabric layer then is transferred to the wet water retention fabric layer, and then the external voltage is transferred to the wearer's skin via the wet water retention fabric layer. Additionally, the wet water retention fabric layer as a whole has the same potential, thus the problem of local thermal points or local spike points can be prevented in the electrode structure of the present disclosure.

It is to be understood that both the foregoing general description and the following detailed description are by examples, and are intended to provide further explanation of the invention as claimed.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention. In the drawings.

DESCRIPTION OF THE EMBODIMENTS

Figure 1:
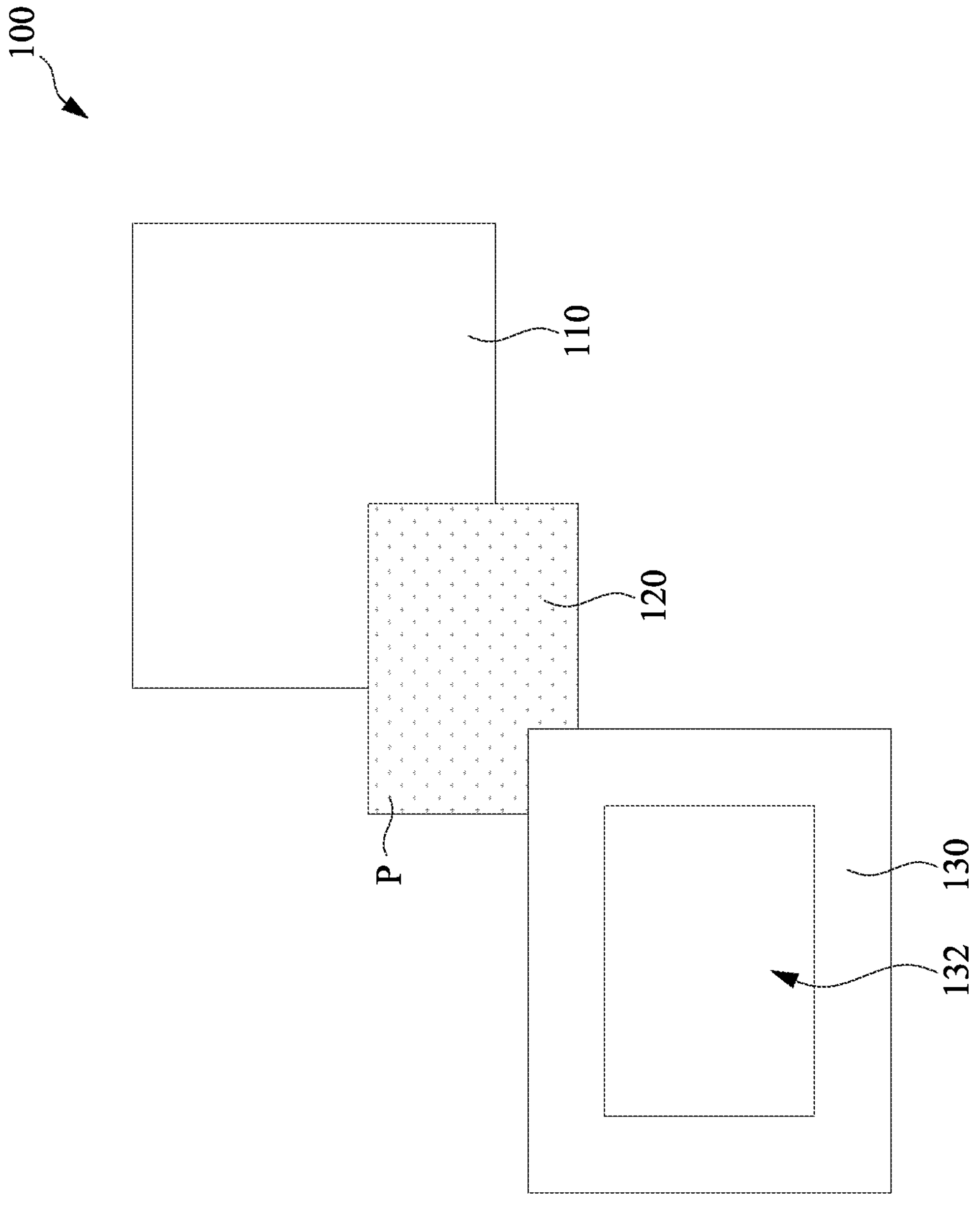
FIG. 1 is a schematic view of an electrode structure for electronic muscle stimulation (EMS) according to some embodiments of the disclosure.

Reference will now be made in detail to the present embodiments of the invention, examples of which are illustrated in the accompanying drawings. Wherever possible, the same reference numbers are used in the drawings and the description to refer to the same or like parts.

Figure 2:
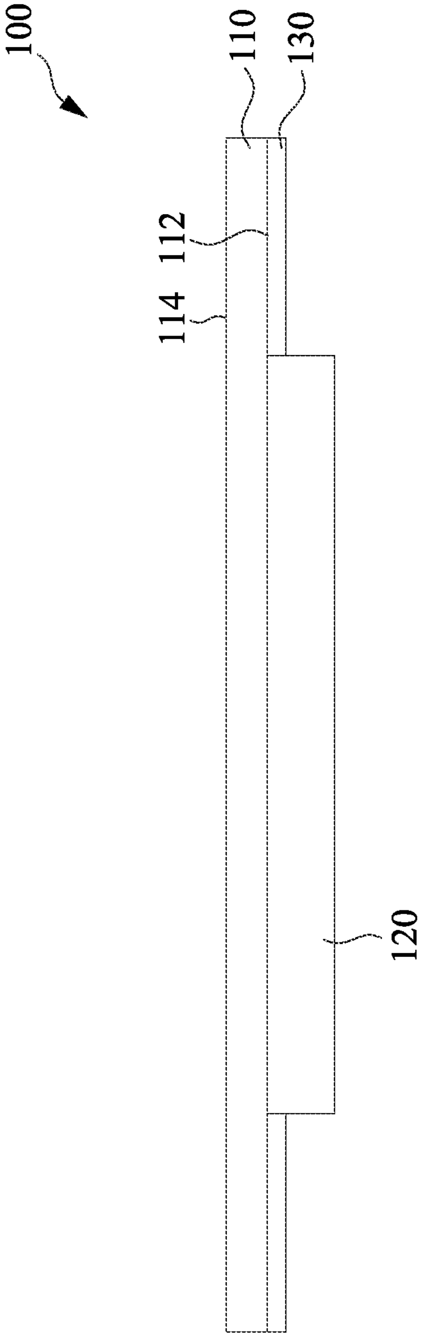
FIG. 2 is a cross-sectional view of the electrode structure for EMS of FIG. 1.

Reference is made to FIG. 1 and FIG. 2. FIG. 1 is a schematic view of an electrode structure for electronic muscle stimulation (EMS) according to some embodiments of the disclosure, and FIG. 2 is a cross-sectional view of the electrode structure for EMS of FIG. 1. The electrode structure 100 includes a conductive fabric layer 110, a water retention fabric layer 120, and a dielectric protection layer 130. The conductive fabric layer 110 has a first surface 112 and a second surface 114 opposite to each other, in which the first surface 112 of the conductive fabric layer 110 facing the wearer's skin. The water retention fabric layer 120 is connected to the first surface 112 of the conductive fabric layer 110. The EMS points P of the electrode structure 100 are consisted of the water retention fabric layer 120. The dielectric protection layer 130 is disposed on the first surface 112 of the conductive fabric layer 110 and surrounding a peripheral of the water retention fabric layer 120. In some embodiments, the material of the dielectric protection layer 130 includes silicon or elastic plastic such as thermoplastic polyurethane (TPU).

In some embodiments, the size of the water retention fabric layer 120 is smaller than the size of the conductive fabric layer 110. The shape of the dielectric protection layer 130 can be a rectangle having an opening 132. The dielectric protection layer 130 covers the first surface 112 of the conductive fabric layer 110, and the water retention fabric layer 120 is exposed from the opening 132 of the dielectric protection layer 130. As a result, when the electrode structure 100 is used during the EMS test, only the water retention fabric layer 120 and the dielectric protection layer 130 contact the wearer's skin, and the conductive fabric layer 110 does not directly contact the wearer's skin. In some embodiments, the thickness of the water retention fabric layer 120 is thicker than the thickness of the dielectric protection layer 130. Therefore, when the electrode structure 100 is worn and in contact with the wearer's skin, the water retention fabric layer 120 is protruded toward the wearer's skin such that the water retention fabric layer 120 can touch the wearer's skin firmly.

The material of the water retention fabric layer 120 has a property that can obviously change the surface resistance of the electrode structure 100 after the water retention fabric layer 120 absorbs moisture, in which the surface resistance of the electrode structure 100 is measured at the portion of the water retention fabric layer 120 exposed by the opening 132 of the dielectric protection layer 130. It is noted that the portion of the water retention fabric layer 120 exposed by the opening 132 of the dielectric protection layer 130 is also served as the portion providing electric stimulation to the wearer's skin.

In some embodiments, the water retention fabric layer 120 has high moisture absorbing and transferring ability. The water retention fabric layer 120 is able to quickly absorb moisture from environment or from skin, and further evenly spreads the moisture in the fibers of the water retention fabric layer 120. A moisture transferring ability of the water retention fabric layer 120 is greater than level 4, following FTTS-FA-004 test method. After the water retention fabric layer 120 absorbs sufficient amount of moisture, the moisture in the water retention fabric layer 120 is ionized by potential difference when an external voltage is applied to the water retention fabric layer 120. The ionization of the moisture in the water retention fabric layer 120 leads to electron flow, and the ionized moisture becomes conductive. As a result, the surface resistance of the water retention fabric layer 120 can be greatly reduced.

Namely, before the water retention fabric layer 120 absorbs moisture, e.g. the water retention fabric layer 120 is dry, the electrode structure 100 has a huge surface resistance such as greater than 100 MΩ, and the water retention fabric layer 120 can be regarded as an insulator. After the water retention fabric layer 120 absorbs sufficient amount of moisture and an external voltage is applied to the water retention fabric layer 120, the potential difference leads to ionization of the moisture, thus the surface resistance of the water retention fabric layer 120 is obviously reduced, and the water retention fabric layer 120 can be regarded as a conductor. The external voltage may enter the water retention fabric layer 120 via the conductive fabric layer 110 and then enter wearer's skin via the water retention fabric layer 120. At this time, the surface resistance of the electrode structure 100 is reduced to a range from 30 kΩ to 100 kΩ.

The surface resistance of the water retention fabric layer 120 changes obviously after the water retention fabric layer 120 absorbs moisture. In some embodiments, the water retention fabric layer 120 can be cotton fibers, modified nylon fibers, alginate fibers, or combinations thereof. For example, the yarn utilized in the water retention fabric layer 120 can be core-spun yarn, in which the shell of the core-spun yarn can be hydrophilic fiber such as modified nylon fibers or alginate fibers, and the core of the core-spun yarn can be cotton fibers, to absorb moisture in the core-spun yarn to achieve the water retention purpose.

The material of the water retention fabric layer 120 is not selected from a conductor. Therefore, the problem of local thermal points or local spike points raised by using conductive fabric as EMS electrode contact plane in the traditional EMS device can be prevented.

Additionally, the water retention fabric layer 120 is directly connected to the conductive fabric layer 110. The external voltage can be gently and indirectly transferred to the wearer's skin through the electrode structure 100. More particularly, the external voltage first enters the conductive fabric layer 110, then enters the wet water retention fabric layer 120, then enters the wearer's skin for EMS. The wet water retention fabric layer 120 as a whole has the same potential, thus the problem of local thermal points or local spike points can be prevented in the electrode structure 100 of the present disclosure.

In some embodiments, the EMS current of the electrode structure 100 is in a range from 1 mA to 100 mA, which is strong enough to induce the corresponding wearer's muscle reaction such as grasp or palm lifting, etc. With the increasing of the EMS current, the angle of wearer's muscle reaction such as the lifting angle of wearer's palm is increased accordingly.

Reference is made to table 1, which shows the fabric dry rates and moisture transferring abilities of different embodiments of the water retention fabric layer 120 of the electrode structure 100 of the present disclosure. The water retention fabric layer 120 may be cotton fibers, alginate fibers and cotton fibers (e.g. the core-spun yarns including alginate fibers and cotton fibers), or modified nylon fibers (e.g. Aquatimo). Embodiments of water retention fabric layer 120 can be formed of different fibers and different weaving forms, and the test results following FTTS-FA-004, including fabric dry rates and moisture transferring abilities, of the embodiments of water retention fabric layer 120 are shown in table 1. According to the measured fabric dry rates, these water retention fabric layer 120 have moisture-containing ratios greater than 50%, which represent that the water retention fabric layers 120 have good moisture-containing abilities. According to the measured moisture transferring abilities, the water retention fabric layers 120 made of alginate fibers and cotton fibers or modified nylon fibers have good moisture transferring abilities and are able to provide uniform conductivities.

Generally, a single cycle of EMS is about 10 minutes to 15 minutes. According to the test result, the moisture-containing abilities of the water retention fabric layers 120 can to keep sufficient amount of moisture for complete the EMS cycle.

TABLE 1

Fabric dry rates and moisture transferring abilities of the embodiments of water retention fabric layers

| | | Cotton fibers 40's | Alginate fibers/Cotton fibers (25%/75%) | modified nylon fibers 70D/48f |
|---|---|---|---|---|
| Bird's eye-weave A | Fabric dry rate (%) (moisture-containing ratio after 40 mins) | 91 | 71 | 74 |
| Bird's eye-weave B | | 88 | 65 | 72 |
| Bird's eye-weave C | | 92 | 88 | 52 |
| Bird's eye-weave A | Moisture transferring ability ($mm^2$) | 70 | 416 | 316 |
| Bird's eye-weave B | | 74 | 632 | 402 |
| Bird's eye-weave C | | 64 | 68 | 793 |

Figure 3:
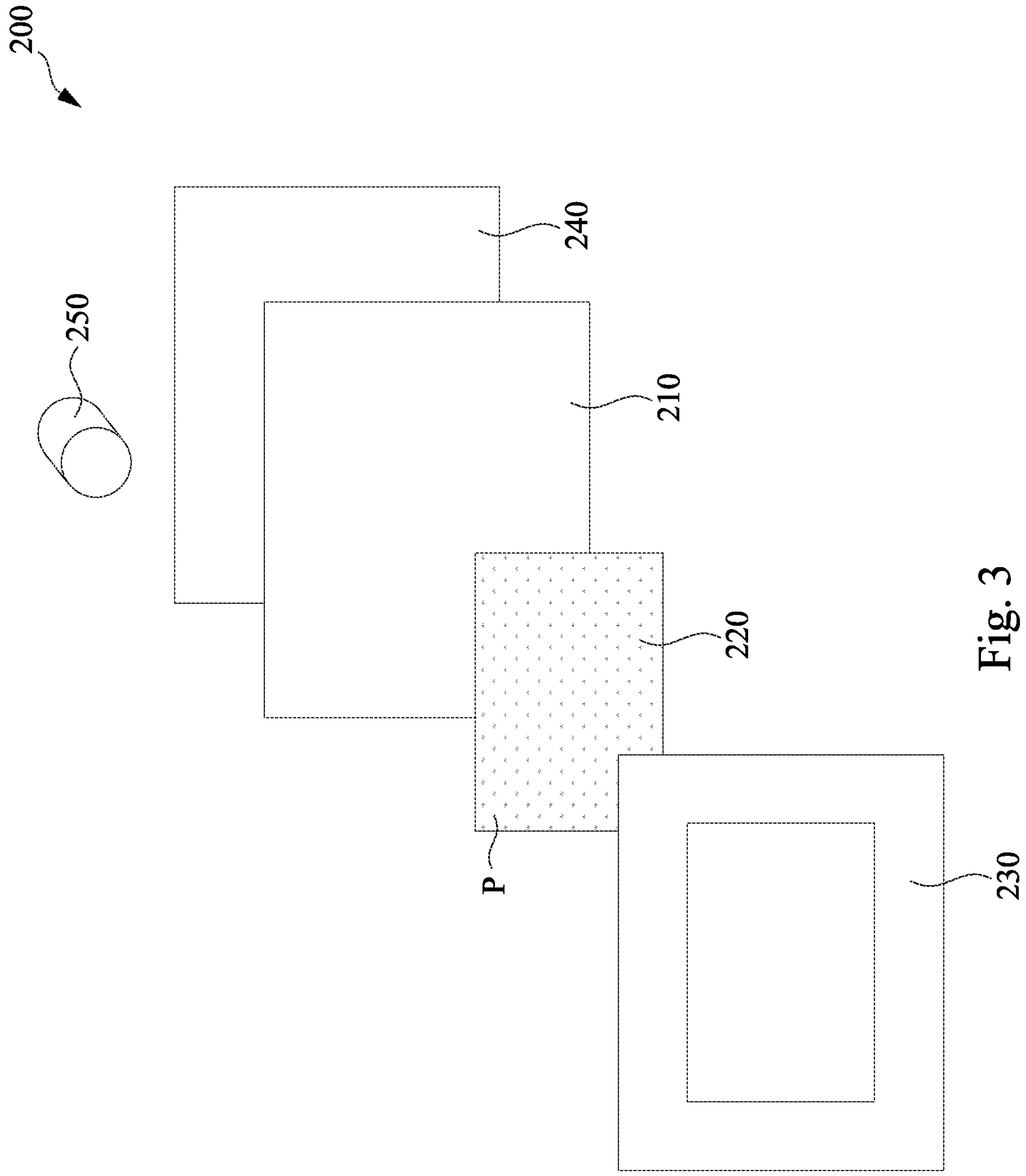
FIG. 3 is a schematic view of an electrode structure for EMS according to some embodiments of the disclosure.
Figure 4:
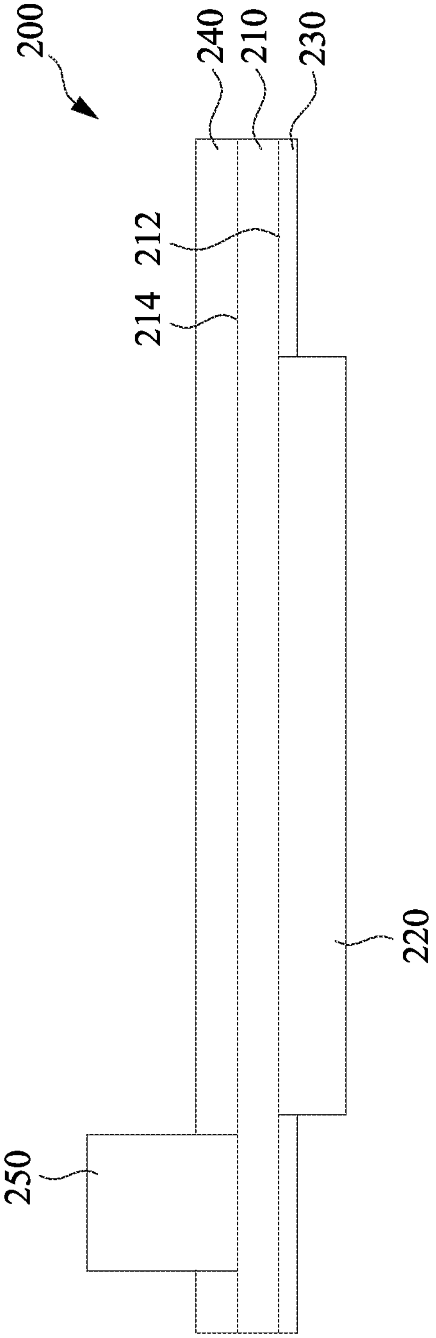
FIG. 4 is a cross-sectional view of the electrode structure for EMS of FIG. 3.

Reference is further made to FIG. 3 and FIG. 4. FIG. 3 is a schematic view of an electrode structure for EMS according to some embodiments of the disclosure, and FIG. 4 is a cross-sectional view of the electrode structure for EMS of FIG. 3. The electrode structure 200 includes a conductive fabric layer 210, a water retention fabric layer 220, a dielectric protection layer 230, a dielectric isolation layer 240, and a conductive contact 250. The conductive fabric layer 210 has a first surface 212 and a second surface 214 opposite to each other, and the water retention fabric layer 220 is connected to the first surface 212 of the conductive fabric layer 210. The EMS points P of the electrode structure 200 are consisted of the water retention fabric layer 220. The dielectric protection layer 230 is disposed on the first surface 212 of the conductive fabric layer 210 and surrounding a peripheral of the water retention fabric layer 220. The dielectric isolation layer 240 is disposed on the second surface 214 of the conductive fabric layer 210. The conductive contact 250 penetrates the dielectric isolation layer 240 and is connected to the conductive fabric layer 210. Thus an external voltage can be provides to the conductive fabric layer 210 via the conductive contact 250.

The external voltage is gently and indirectly transferred to the wearer's skin through plural layers within the electrode structure 200. The external voltage first enters the conductive fabric layer 210 via the conductive contact 250. Then the external voltage enters the wet water retention fabric layer 220 through the conductive fabric layer 210 and then enters wearer's skin via the water retention fabric layer 220 for EMS. In order to improve the moisture-containing ability of the water retention fabric layer 220, the dielectric isolation layer 240 is disposed on the second surface 214 of the conductive fabric layer 210 of the electrode structure 200, to keep the moisture in the wet water retention fabric layer 220.

In some embodiments, the material of the dielectric protection layer 240 includes silicon or elastic plastic such as TPU. The materials of the dielectric protection layer 240 and the dielectric protection layer 230 can be the same or different. In some embodiments, the dielectric protection layer 240 is detachably assembled to the conductive fabric layer 210 such as jacketing or wrapping on the conductive fabric layer 210. Thus the electrode structure 200 can be free of damaged by the moisture environment while storing the electrode structure 200 not in EMS use.

In some embodiments, the conductive contact 250 is a metal plug or a metal pillar. The corresponding host can be coupled to or clamped to the metal plug or the metal pillar conductive contact 250 through a fastener or a clamp. The external voltage provided by the host is transferred to the conductive contact 250, and is transferred to the conductive fabric layer 210 via the conductive contact 250. Then the external voltage is transferred to the wet water retention fabric layer 220 through the conductive fabric layer 210. The wet water retention fabric layer 220 is in contact with the wearer's skin such that the external voltage is transferred to the wearer's skin for EMS.

Figure 5:
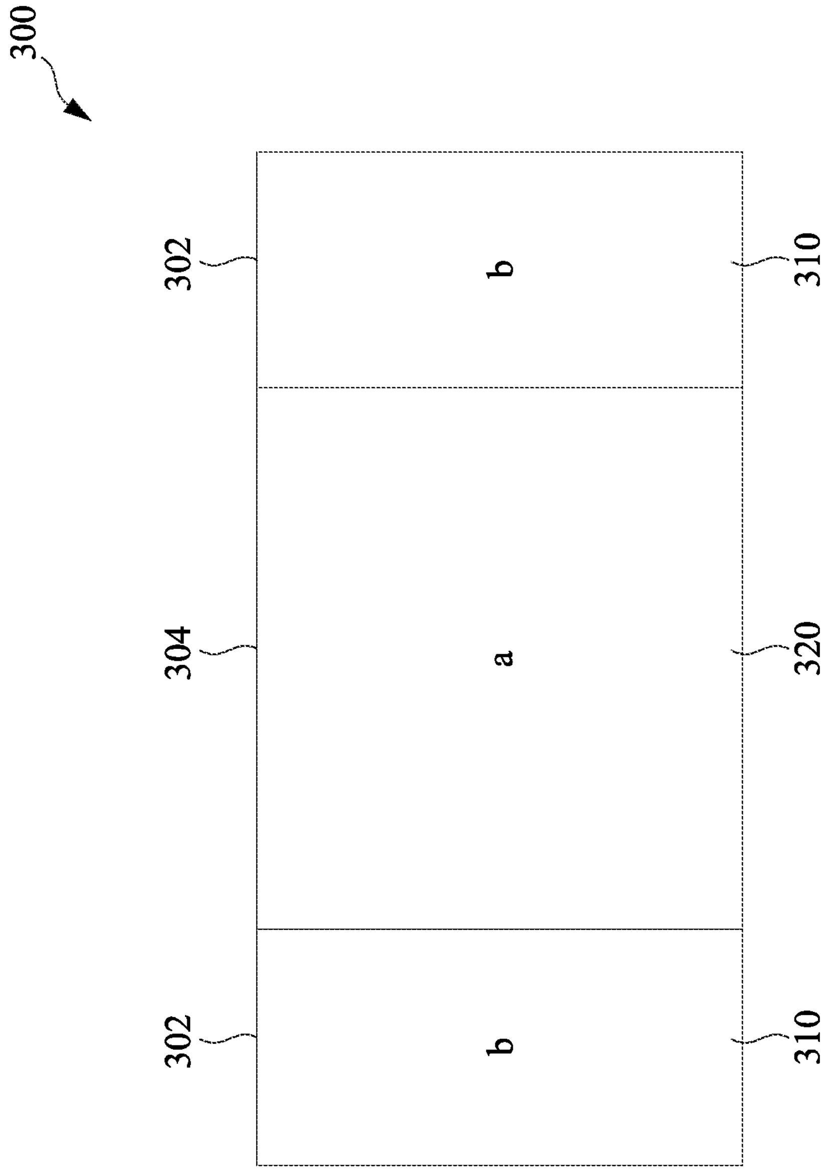
FIG. 5 is an arrangement of the conductive fabric layer and the water retention fabric layer of the electrode structure according to some embodiments of the disclosure.

Reference is made to FIG. 5, which is an arrangement of the conductive fabric layer and the water retention fabric layer of the electrode structure according to some embodiments of the disclosure. The conductive fabric layer 310 and the water retention fabric layer 320 can be integrately formed by a weaving process. For example, the electrode structure 300 has first regions 302 and a second region 304, in which the second region 304 is between the first regions 302. The first regions 302 are formed by conductive fibers, and the second region 304 is formed by conductive fibers and water retention fibers. The rectangle dielectric isolation layer with an opening (not shown) is further sealed thereon. The dielectric isolation layer covers the first regions 302 and peripheral of the second region 304 and allows a portion of the second region 304 exposing from the opening of the dielectric isolation layer.

It is noted that on the inner side of the electrode structure 300, only the water retention fibers are revealed at the second region 304, and the conductive fibers are hidden under the water retention fibers. For example, the conductive fabric layer 310 and the water retention fabric layer 320 can be formed by flat knitting, in which the water retention yarn loops of the water retention fabric layer 320 and the conductive yarn loops of the conductive fabric layer 310 are interconnected at the second region 304, and the conductive yarn loops are completely hidden under the water retention yarn loops of the water retention fabric layer 320.

Figure 6:
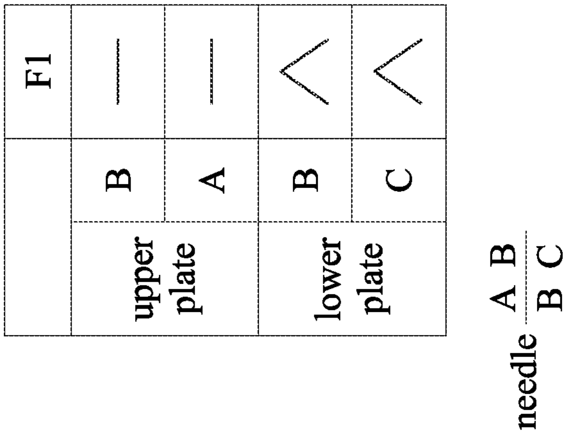
FIG. 6 and FIG. 7 are the knitting rules of forming the first regions and second region of FIG. 5.
Figure 7:
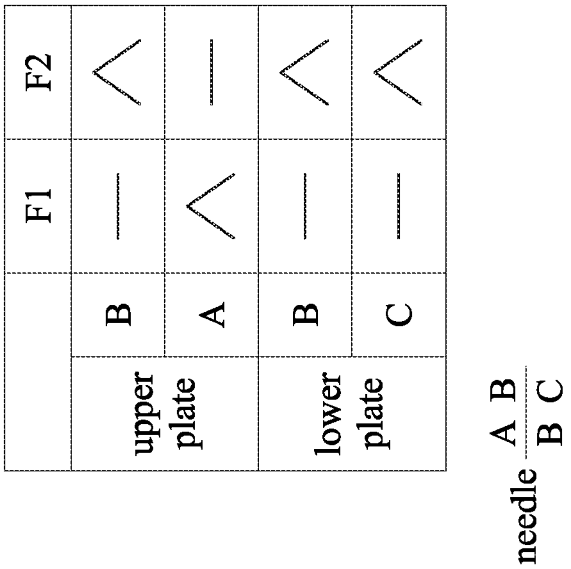

Reference is made to FIG. 6 and FIG. 7, which are the knitting rules of forming the first regions and second region of FIG. 5. The first regions 302 in FIG. 5 are formed by the knitting rule disposed in FIG. 6. The sequence of the needle plate and the operation of the needles are shown in FIG. 6, in which "A" represents forming a yarn loop, and F1 is a conductive yarn. The second region 304 in FIG. 5 is formed by the knitting rule disposed in FIG. 7. The sequence of the needle plate and the operation of the needles are shown in FIG. 7, in which "/\" and "\/" both represent forming a yarn loop, F1 is a conductive yarn, and F2 is a water retention yarn.

In some embodiments, the water retention fibers can be cotton fibers, modified nylon fibers, alginate fibers, or combinations thereof. The water retention fibers can be single core yarns or core-spun yarns. In some embodiments, the conductive fibers can be fibers including metal wires or fibers coated with a metal layer. The metal utilized in the conductive fibers can be Au, Ag, Cu, Ni, Cr, or alloys thereof.

Figure 8:
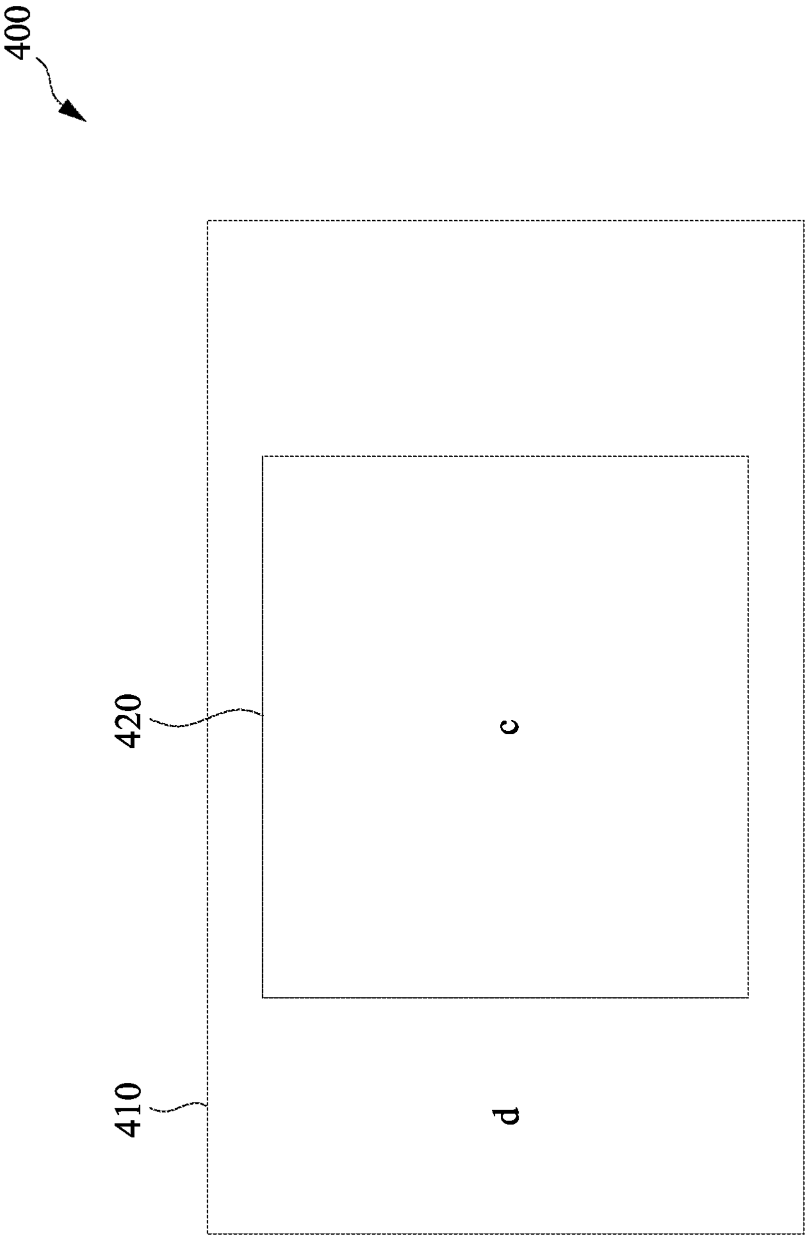
FIG. 8 is an arrangement of the conductive fabric layer and the water retention fabric layer of the electrode structure according to some other embodiments of the disclosure.

Reference is made to FIG. 8, which is an arrangement of the conductive fabric layer and the water retention fabric layer of the electrode structure according to some other embodiments of the disclosure. The conductive fabric layer 410 and the water retention fabric layer 420 of the electrode structure 400 can be formed separately, and then the conductive fabric layer 410 and the water retention fabric layer 420 are combined. For example, the conductive fabric layer 410 cane be a fabric comprising conductive yarns or metal wires, or the conductive fabric layer 410 can be a non-woven fabric coated with a conductive layer. The water retention fabric layer 420 can be a fabric or a non-woven fabric made of cotton fibers, modified nylon fibers, alginate fibers, or combinations thereof. The water retention fabric layer 420 can be combined with the conductive fabric layer 410 by a needling punching process.

The rectangle dielectric isolation layer with an opening (not shown) is further sealed thereon. The dielectric isolation layer covers an edge of the water retention fabric layer 420 and allows a portion of the water retention fabric layer 420 exposing from the opening of the dielectric isolation layer. Because the edge of the water retention fabric layer 420 is sandwiched between the dielectric isolation layer and the conductive fabric layer 410, the binding of the conductive fabric layer 410 and the water retention fabric layer 420 is secured to prevent unwanted delamination.

According to above embodiments, the present disclosure provides an electrode structure to gently and indirectly transfer an external voltage to the wearer's skin. The EMS points of the electrode structure are consisted of the water retention fabric layer. The external voltage enters the conductive fabric layer then is transferred to the wet water retention fabric layer, and then the external voltage is transferred to the wearer's skin via the wet water retention fabric layer. Additionally, the wet water retention fabric layer as a whole has the same potential, thus the problem of local thermal points or local spike points can be prevented in the electrode structure of the present disclosure.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. An electrode structure for electronic muscle stimulation (EMS), comprising:

a conductive fabric layer having a first surface and a second surface opposite to each other;

a plurality of EMS points on the first surface of the conductive fabric layer;

a water retention fabric layer connected to the first surface of the conductive fabric layer, wherein the plurality of EMS points are consisted of the water retention fabric layer, wherein the water retention fabric layer and the conductive fabric layer are interconnected by a plurality of water retention yarn loops of the water retention fabric layer and a plurality of conductive yarn loops of the conductive fabric layer, and the conductive yarn loops are completely hidden under the water retention yarn loops; and a dielectric protection layer disposed on the first surface of the conductive fabric layer and surrounding a peripheral of the water retention fabric layer.

2. The electrode structure of claim 1, wherein the electrode structure has a surface resistance ranging from 30 kΩ to 100 Ω, after the electrode structure absorbs moisture.

3. The electrode structure of claim 1, wherein the electrode structure is configured to deliver an EMS current, and the EMS current is in a range from 1 mA to 100 mA.

4. The electrode structure of claim 1, further comprising a dielectric isolation layer disposed on the second surface of the conductive fabric layer.

5. The electrode structure of claim 4, further comprising a conductive contact penetrating the dielectric isolation layer and connecting to the conductive fabric layer such that a voltage is applied to the conductive fabric layer via the conductive contact.

6. The electrode structure of claim 1, wherein the conductive fabric layer is a fabric comprising conductive yarns or metal wires, or a non-woven fabric coated with a conductive layer.

7. The electrode structure of claim 1, wherein the water retention fabric layer comprises cotton fibers, modified nylon fibers, alginate fibers, or combinations thereof.

8. The electrode structure of claim 1, wherein the dielectric protection layer comprises silicon or elastic plastic.

9. The electrode structure of claim 1, wherein a moisture transferring ability of the water retention fabric layer is greater than grade 4, following FTTS-FA-004 test method.

* * * * *